United States Patent [19]

Schmidt et al.

[11] Patent Number: 4,507,483

[45] Date of Patent: Mar. 26, 1985

[54] 3-[(SUBSTITUTED-AMINO)(THIENYL)METHYL]-1H-INDOLES

[75] Inventors: Paul J. Schmidt, Sharonville; William M. Hung, Cincinnati, both of Ohio

[73] Assignee: The Hilton-Davis Chemical Co., Cincinnati, Ohio

[21] Appl. No.: 473,760

[22] Filed: Mar. 9, 1983

Related U.S. Application Data

[62] Division of Ser. No. 341,951, Jan. 22, 1982, Pat. No. 4,398,030, which is a division of Ser. No. 127,650, Mar. 6, 1980, Pat. No. 4,341,402.

[51] Int. Cl.³ .................. C07D 409/14; C07D 409/06; C07D 403/14; B41M 5/16; B41M 5/18; B41M 5/22

[52] U.S. Cl. .................... 546/201; 548/468; 548/506; 544/143; 287/27.5; 427/151; 428/320.4; 428/320.6; 428/488; 428/537; 428/913; 428/914; 428/307; 428/411; 424/537; 424/320.8; 430/200; 430/348; 430/394; 106/21

[58] Field of Search ........................ 546/201; 548/468

[56] References Cited

U.S. PATENT DOCUMENTS 3,958,815  5/1976  Poot et al. .................... 282/27.5
4,257,954  3/1981  Schmidt et al. ................ 548/468
4,341,402  7/1982  Schmidt et al. ................ 548/468
4,398,030  8/1983  Schmidt et al. ................ 546/201

FOREIGN PATENT DOCUMENTS 1561663  3/1969  France ............................ 548/468

OTHER PUBLICATIONS

M. Scholtz, Chem. Ber. 46, 2138-2146, (1913).
R. W. Huffman et al., J. Amer. Chem. Soc. 89, 6243-6251, (1967).
C. W. Rees et al., J. Chem. Soc., 687-691, (1965).
Chem. Abstracts, vol. 75, Item 88430x, (1974), abstracting V. N. Rusinova et al., Tr. Mosk. Khim-Tekknol. Inst., No. 66, 125-128, (1970).

Primary Examiner—Robert T. Bond
Attorney, Agent, or Firm—Paul E. Dupont; B. Woodrow Wyatt

[57] ABSTRACT

3-[(Substituted-amino)(aryl or heteroaryl)methyl]-1H-indoles which are useful as color-formers in pressure-sensitive carbonless duplicating systems and thermal marking systems are prepared by reacting 3-[(arylsulfonyl)(aryl or heteroaryl)methyl]-1H-indoles with amines or precursors thereof in the presence of a base.

1 Claim, No Drawings

3-[(SUBSTITUTED-AMINO)(THIENYL)METHYL]-1H-INDOLES

CROSS-REFERENCE TO RELATED APPLICATIONS

This application is a division of application Ser. No. 341,951 filed Jan. 22, 1982, now U.S. Pat. No. 4,398,030 issued Aug. 9, 1983, in turn a division of application Ser. No. 127,650 filed Mar. 6, 1980, now U.S. Pat. No. 4,341,402 issued July 27, 1982.

BACKGROUND OF THE INVENTION

1. Field of the Invention

The present invention relates to a group of compounds classified in the field of organic chemistry as 3-[(substituted-amino)(aryl or heteroaryl)methyl]-1H-indoles which are useful as color formers in pressure-sensitive carbonless duplicating systems and thermal marking systems; to processes for the preparation thereof and to pressure-sensitive carbonless duplicating systems and thermal marking systems containing the same.

2. Description of the Prior Art

Several classes of organic compounds of widely diverse structural types are known to be useful as color formers for carbonless duplicating systems. Among the most widely recognized classes are the phenothiazines, for example, benzoyl leuco methylene blue; fluorans, for example, 2'-anilino-6'-diethylaminofluoran; phthalides, for example, crystal violet lactone; methine dyes, for example, Michler's hydrol and derivatives thereof and various other types of color formers currently employed in commercially accepted carbonless duplicating systems. Typical of the many such systems taught in the prior art are those described in U.S. Pat. Nos. 2,712,507, 2,800,457 and 3,041,289, which issued July 5, 1955, July 23, 1957 and June 26, 1962, respectively. Many of the color formers in the prior art suffer one or more disadvantages such as low tinctorial strength, poor light stability, poor xerographic copiability, low resistance to sublimation, and low solubility in common organic solvents, the latter disadvantage thus requiring the use of specialized and expensive solvents in order to obtain microencapsulated solutions of sufficient concentration for use in pressure-sensitive copying systems.

The following appear to constitute the most relevant prior art relative to the present invention.

U.S. Pat. No. 3,958,815 issued May 25, 1976 discloses in most pertinent part a group of compounds stated to be useful as dye precursors in pressure-sensitive recording materials and having the formula:

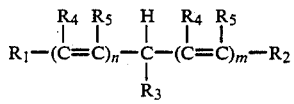

wherein inter alia $R_1$ and $R_2$ represent (1) an aryl group substituted with an ether group $R_6$—O— in which $R_6$ represents a hydrocarbon group or (2) a heterocyclic group; $R_3$ represents $NR_8R_9$ in which each of $R_8$ and $R_9$ (same or different) represents hydrogen or an alkyl group, a cycloalkyl group, an aralkyl group or an aryl group, or $R_8$ and $R_9$ together represent the necessary atoms to close a nitrogen-containing heterocyclic nucleus, and m and n are 0.

French Pat. No. 1,561,663 published March 28, 1969 discloses in most pertinent part a series of compounds having the formula:

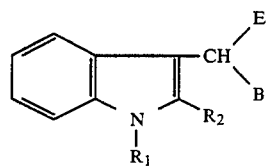

wherein inter alia $R_1$ and $R_2$ are independently hydrogen, alkyl or aryl; B is a carbocyclic or heterocyclic ring system, and E is amino, substituted amino such as alkylamino or arylamino, or piperidino. The compounds are stated to be useful as intermediates in the preparation of triphenylmethane dyes.

M. Scholtz, Chem. Ber. 46, 2138–2146 (1913), discloses o-hydroxyphenyl-piperidino-α-methylindolyl-methane and [2-hydroxy-5-methyl-phenyl]-piperidino-α-methylindolyl-methane prepared by reacting salicylaldehyde or p-homosalicylaldehyde with α-methylindole and piperidine. No utility is disclosed for these compounds.

R. W. Huffman and T. C. Bruice, J. Amer. Chem. Soc. 89, 6243–6251 (1967), disclose phenyl-3-(2-methylindolyl)morpholinomethane and phenyl-3-(2-methylindolyl)piperidinomethane as reaction products in a kinetic study.

C. W. Rees and C. R. Sabet, J. Chem. Soc., 687–691 (1965), disclose 3-(α-anilinobenzyl)-2-methylindole. No utility is disclosed for the compound.

V. N. Rusinova et al., Tr. Mosk, Khim.-Tekhnol. Inst. No. 66, 125–128 (1970); Chem. Abstracts 75, 88430x (1971), disclose 3-[(methylamino)(phenyl)methyl]indole. No utility is disclosed for the compound.

SUMMARY OF THE INVENTION

The present invention provides certain novel 1-$R_1$-2-$R_2$-3-[($R_3R_4$N)(Z)methyl]-1H-indoles which are useful as color formers in pressure-sensitive carbonless duplicating systems and thermal marking systems. The compounds develop colored images of good tinctorial strength and have the advantage of good xerographic copiability and enhanced solubility in common organic solvents.

This invention also provides a novel process for preparing the above-described novel 1-$R_1$-2-$R_2$-3-[($R_3R_4$N)(Z)methyl]-1H-indoles as well as certain known related compounds which comprises reacting a 1-$R_1$-2-$R_2$-3-[(R-phenylsulfonyl)(Z)methyl]-1H-indole with an amine $R_3R_4$NH or a precursor thereof in the presence of an alkali metal hydroxide.

The invention further provides as an article of manufacture a pressure-sensitive carbonless duplicating system or thermal marking system which contains a support sheet coated with a color-forming substance comprising a 1-$R_1$-2-$R_2$-3-[($R_3R_4$N)(Z)-methyl]-1H-indole.

DETAILED DESCRIPTION OF THE INVENTION INCLUSIVE OF THE PREFERRED EMBODIMENTS

More specifically the invention sought to be patented resides, in a composition of matter aspect, in 1-$R_1$-2-$R_2$-3-[($R_3R_4$N)(Z)methyl]-1H-indoles which are useful as color formers in pressure-sensitive carbonless duplicating systems and thermal marking systems and which have Formula I:

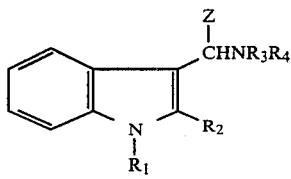

Formula I wherein:
$R_1$ is hydrogen or lower-alkyl;
$R_2$ is hydrogen, lower-alkyl or phenyl;
$R_3$ is hydrogen or lower-alkyl;
$R_4$ is hydrogen, lower-alkyl, benzyl, di-lower-alkylamino-lower-alkyl, tri-lower-alkylammonium-lower-alkyl, phenyl, phenyl substituted with 1 or 2 halo, lower-alkyl or lower-alkoxy groups or $NR_3R_4$ is pyrrolidino, piperidino, hexamethyleneimino or morpholino; and
Z is biphenylyl, naphthyl or a substituent having the formula

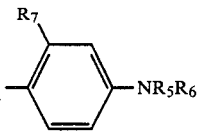

wherein
$R_5$ and $R_6$ are independently lower-alkyl or benzyl, and
$R_7$ is hydrogen, lower-alkyl, lower-alkoxy, halo or di-lower-alkylamino.

In another composition of matter aspect the invention sought to be patented resides in compounds of Formula I above useful as color formers in pressure-sensitive carbonless duplicating systems and thermal marking systems, wherein in said formula
$R_1$, $R_2$, $R_3$ and $R_4$ have the previously given meanings, and
Z is a substituent having the formula

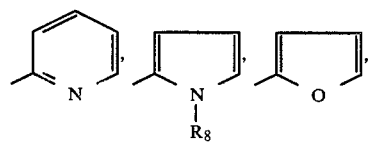

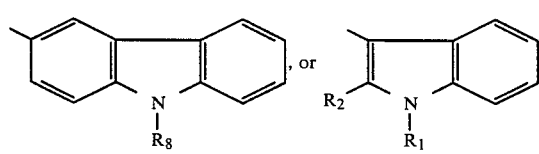

wherein $R_8$ is hydrogen or lower-alkyl.

A further composition of matter aspect of the invention sought to be patented resides in a compound, useful as a color former in pressure-sensitive carbonless duplicating systems and thermal marking systems, selected from the group consisting of:
3-[(dimethylamino)(2-thienyl)methyl]-1-ethyl-2-methyl-1H-indole and
3-[(1-piperidinyl)(2-thienyl)methyl]-1-ethyl-2-methyl-1H-indole.

Preferred embodiments of this invention are compounds of Formula I hereinabove wherein:
$R_1$, $R_2$, $R_3$ and $R_4$ have the previously given meanings, and
Z is a substituent having the formula

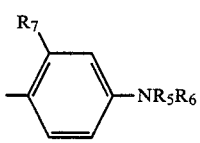

wherein $R_5$ and $R_6$ have the previously given meanings and $R_7$ is hydrogen. These compounds are especially valuable because they are obtained from inexpensive and readily available starting materials.

In an article of manufacture aspect the invention sought to be patented resides in a pressure-sensitive carbonless duplicating system or thermal marking system containing a support sheet coated with a color-forming substance comprising a compound having Formula I hereinabove wherein:
$R_1$, $R_2$, $R_3$ and $R_4$ have the previously given meanings, and
Z is biphenylyl, naphthyl or a substituent having the formula:

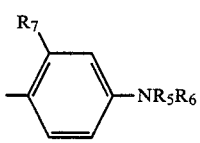

wherein
$R_5$ and $R_6$ are independently lower-alkyl or benzyl, and
$R_7$ is hydrogen, lower-alkyl, lower-alkoxy, halo or di-lower-alkylamino.

In another article of manufacture aspect the invention sought to be patented resides in a pressure-sensitive carbonless duplicating system or a thermal marking system containing a support sheet coated with a color-forming substance comprising a compound having Formula I hereinabove wherein:
$R_1$, $R_2$, $R_3$ and $R_4$ have the previously given meanings, and
Z is a substituent having the formula:

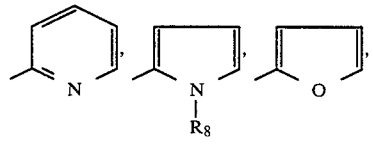

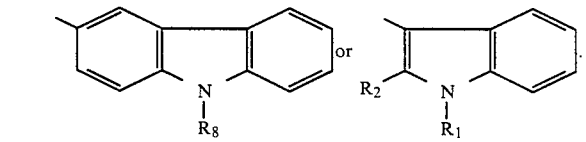

In yet a further article of manufacture aspect the invention sought to be patented resides in a pressure-sensitive carbonless duplicating system or a thermal marking system containing a support sheet coated with a color-forming substance comprising a compound selected from the group consisting of:

3-[(dimethylamino)(2-thienyl)methyl]-1-ethyl-2-methyl-1H-indole and

3-[(1-piperidinyl)(2-thienyl)methyl]-1-ethyl-2-methyl-1H-indole.

Preferred pressure-sensitive carbonless duplicating systems or thermal marking systems of the present invention are those which contain a color-forming substance comprising a compound of Formula I wherein:

$R_1$, $R_2$, $R_3$ and $R_4$ have the previously given meanings; and

Z is a substituent having the formula

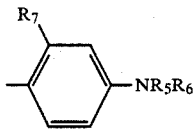

where $R_5$ and $R_6$ have the above-given meanings and $R_7$ is hydrogen.

In its process aspect the invention sought to be patented resides in a process for producing a compound having Formula I which comprises reacting a compound having Formula II

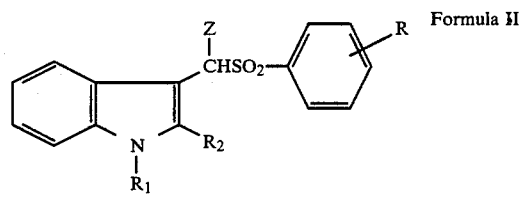

Formula II with an amine having Formula III $R_3R_4NH$ Formula III or a derivative thereof which produces said amine under the conditions of the reaction, in the presence of an alkali metal hydroxide wherein in said formulas:

R is hydrogen or lower-alkyl;

$R_1$, $R_2$, $R_3$ and $R_4$ have the previously given meanings, and

Z is biphenylyl, naphthyl or a substituent having the formulas:

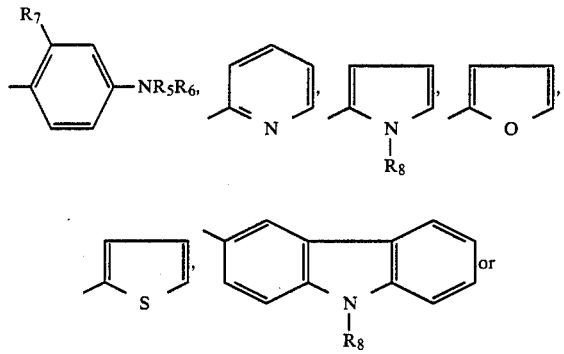

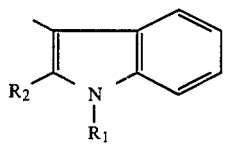

where in the above formulas:

$R_5$ and $R_6$ are independently lower-alkyl or benzyl;

$R_7$ is hydrogen, lower-alkyl, lower-alkoxy, halo or di-lower-alkylamino, and $R_8$ is hydrogen or lower-alkyl.

As used herein the terms "lower-alkyl", "lower-alkoxy" and "di-lower-alkylamino-" denote saturated acyclic groups having from 1 to 4 carbon atoms which may be straight or branched as exemplified by methyl, ethyl, propyl, isopropyl, butyl, sec-butyl, isobutyl, t-butyl, methoxy, ethoxy, propoxy, isopropoxy, butoxy, sec-butoxy, isobutoxy, t-butoxy, dimethylamino, diethylamino, ethylmethylamino, dipropylamino, dibutylamino, isobutylmethylamino, t-butylmethylamino and the like.

The term "tri-lower-alkyl-ammonium-lower-alkyl" signifies an amino-lower-alkyl radical in which the nitrogen atom is substituted by three sterically compatible lower-alkyl groups.

As used herein "halo" is intended to include chloro, fluoro, bromo and iodo, an "alkali metal hydroxide" includes lithium, sodium and potassium hydroxide.

The novel compounds of Formula I hereinabove are essentially colorless in the depicted form. When contacted with an acidic medium, for example silica gel or one of the types ordinarily employed in pressure-sensitive carbonless duplicating systems such as silton clay or phenolic resin, the compounds of Formula I develop a yellow to deep purple image of good to excellent tinctorial strength and possess excellent xerographic copiability and enhanced solubility in common organic solvents. The compounds are thus highly suitable for use as colorless precursors, that is, color-forming substances in pressure-sensitive carbonless duplicating systems. Compounds producing purple colors can be used alone as color formers to produce images which are readily copiable whereas the compounds which produce a yellow to red color can be used as toners in admixture with other color formers to produce images of a neutral shade which desirably are readily copiable by xerographic means.

The compounds of this invention may be incorporated in any of the commercially accepted systems known in the carbonless duplicating art. A typical technique for such application is as follows: solutions containing one or more colorless precursor compounds of Formula I optionally in admixture with other color formers in suitable solvents are microencapsulated by well-known procedures, for example, as described in U.S. Pat. Nos. 3,649,649, 3,429,827 and 4,000,087. The microcapsules are coated on the reverse side of a transfer sheet with the aid of a suitable binder. The coated transfer sheet is then assembled in a manifold with the microcapsule-coated side in contact with a receiving sheet coated with an electron accepting substance for example, silton clay or phenolic resin. Application of pressure to the manifold such as that exerted by a stylus, typewriter or other form of writing or printing, causes the capsules on the reverse side to rupture. The solution of the color former released from the ruptured microcapsules flows to the receiving sheet and on contact with the acidic medium thereon forms a yellow to purple image of good tinctorial strength. It is, of course, obvious that variants of this mode of application can be utilized, for example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers, for example, bisphenol A as described in U.S. Pat. No. 3,539,375, that is, papers which produce a colored image when contacted with a heated stylus or heated type, heating of the mixture produces a colored image of varying shades from yellow to purple, depending on the particular compound of the invention employed. The ability of the compounds of Formula I to form a deep color when heated in admixture with an acidic developer such as bisphenol A makes them useful in thermal paper marking systems either where an original or a duplicate copy is prepared by contacting the thermal paper with a heated stylus or a heated type in any of the methods generally known in the art.

The compounds of this invention which are soluble in water or lower-alkanols, for example, the compounds of Formula I wherein $R_4$ is tri-lower-alkylammonium-lower-alkyl may be incorporated in any of the commercial hectographic or spirit reproducing copying systems such as described in British Pat. No. 1,427,318 published March 10, 1976. In such systems a transfer sheet coated on one side with a layer containing one or more water- or lower-alkanol-soluble color formers of Formula I is placed with its coated surface against one surface of a master paper which is then typed, written or marked on, causing transfer of the coating as a substantially colorless reverse image to the master paper at the points where the transfer sheet and master paper have been pressed together. The master paper is then brought into contact with a succession of sheets of paper moistened with a suitable spirit-reproducing fluid such as ethanol.

In accordance with the aforementioned process aspect of this invention, $1-R_1-2-R_2-3-[(R_3R_4N)(Z)$methyl]-1H-indoles of Formula I are obtained by reacting a R-phenylsulfonyl compound of Formula II with an amine of Formula III or a derivative thereof which produces the amine under the reaction conditions in the presence of an alkali metal hydroxide at a temperature of about 20°–150° C. for approximately 1 to 24 hours. The reaction is conveniently carried out in the presence of aqueous sodium hydroxide from about 40° C. to the reflux temperature of the reaction mixture for approximately 1 to 5 hours.

Although an amine of Formula III can be used directly in the instant process, it is often advantageous, particularly in the case of volatile, low-boiling amines such as dimethylamine, to use an appropriate derivative thereof such as the corresponding formamide, acetamide, symmetrical urea and the like, which under the alkaline hydrolytic conditions of the reaction medium will produce the desired amine in situ. Ordinarily, the formamides are preferred because of their ready availability and relatively facile hydrolysis.

A $1-R_1-2-R_2-3-[(R_3R_4N)(Z)$methyl]-1H-indole obtained in accordance with the above process can be isolated by filtration if it is insoluble in the reaction medium or by dilution of the reaction medium with a miscible solvent in which the product is insoluble, such as water, a lower-alkanol or a low molecular weight hydrocarbon, for example, hexane, in order to effect precipitation of the product. Alternatively, the reaction mixture can be poured into water and the product extracted with an organic solvent such as benzene or toluene, followed by evaporation of the organic solvent leaving the product as a residue. The product once isolated can be purified by conventional means such as trituration or recrystallization from a suitable solvent.

The 3-[(R-phenylsulfonyl)(Z)methyl]-1H-indoles of Formula II which are required as starting materials in the above-described process are obtained by reacting approximately equimolar amounts of an appropriate $1-R_1-2-R_2$-1H-indole, an appropriate aldehyde Z—CHO and an R-phenylsulfinic acid (R, $R_1$, $R_2$ and Z having the previously given meanings) in the presence of an acid catalyst such as hydrochloric acid, in a suitable solvent, for example N,N-dimethylformamide, or a lower-alkanol such as methanol, ethanol or 2-propanol at a temperature of about 5°–150° C. for approximately 1 to 35 hours. The reaction is usually carried out in ethanol at about 5°–60° C. for approximately 1 to 4 hours. The product thus obtained can be isolated by filtration if it is insoluble in the reaction medium or by the addition of a basic substance, for example, triethanolamine or ammonium hydroxide to effect precipitation of the product. Alternatively, the reaction mixture can be poured into water or dilute aqueous base, for example, ammonium hydroxide, sodium hydroxide, sodium carbonate or sodium bicarbonate and the product extracted with an organic solvent, such as benzene, chlorobenzene or toluene followed by evaporation of the organic solvent leaving the product as a residue. The product, once isolated, can be purified by conventional means such as trituration, recrystallization or slurrying in a suitable organic solvent.

The $1-R_1-2-R_2$-1H-indoles as well as the aromatic or heterocyclic aldehydes Z—CHO which are starting materials for preparing the 3-[(R-phenylsulfonyl)(Z)methyl]-1H-indoles of Formula II constitute well-known classes of compounds many of which are commercially available or readily obtained by conventional syntheses well known in the art.

The R-phenylsulfinic acids which are also required as starting materials for the intermediates of Formula II likewise belong to an old and well-known class of compounds. Sulfinic acids are known to be unstable and cannot be stored for long periods of time. Accordingly, in the above-described reaction the sulfinic acid is generated in situ by acidifying an alkali metal R-phenylsulfinate which in turn is readily obtained by conventional procedures, for example, by reacting an R-phenylsulfonyl chloride with sodium sulfite and sodium bicarbonate in water. The sodium R-phenylsulfinate is stable and can be stored until needed. The R-phenylsulfonyl chlorides are, of course, readily available from the interaction of an R-phenylsulfonic acid or salt thereof with phosphorus oxychloride.

The amines of Formula III or precursors thereof such as the corresponding formamides, acetamides and symmetrical ureas belong to well-known classes of compounds and are generally commercially available or can be obtained by conventional means from readily available starting materials.

The molecular structures of the compounds of this invention were assigned on the basis of the modes of synthesis and study of their infrared and nuclear magnetic resonance spectra.

The following examples will further illustrate the invention without, however, limiting it thereto.

EXAMPLE 1

A. To a stirred mixture containing 175.0 ml. of ethyl alcohol, 27.5 ml. of concentrated hydrochloric acid, 30.4 g. of 86.4% sodium p-toluenesulfinate and 18.5 g. of p-(dimethylamino)benzaldehyde chilled to approximately 5° C. was slowly added 19.5 g. of 91.2% 1-ethyl-2-methyl-1H-indole. The resulting mixture was stirred approximately 3.5 hours at room temperature during which period the color changed from blue to yellow. The pH of the mixture was adjusted to approximately 8 by the addition of 40.0 g. of triethanolamine and after stirring approximately 20 minutes at room temperature the temperature was raised to and maintained at 55°–60° C. for approximately 20 minutes. After cooling to about 10° C. the resulting pink solid was collected by filtration and washed with 100 ml. of cold ethyl alcohol. The solid was then suspended in a mixture of 350 ml. of water and 10 g. of triethanolamine at room temperature for approximately 30 minutes, collected by filtration, washed successively with 150 ml. portions of 3% aqueous triethanolamine and water and dried under vacuum at 40° C. to give 42.2 g. of 3-{[4-(dimethylamino)phenyl](4-methylphenylsulfonyl)methyl}-1-ethyl-2-methyl-1H-indole which softened at 155° C. and melted at 159°–161° C.

B. To a stirred mixture containing 3.5 g. of 3-{[4-(dimethylamino)phenyl](4-methylphenylsulfonyl)methyl}-1-ethyl-2-methyl-1H-indole, 20 ml. of diethylamine and 25 ml. of dimethylsulfoxide was added 1.5 g. of potassium hydroxide. After stirring 20 hours at room temperature, the reaction mixture was quenched in 300 ml. of ice-water, the resulting precipitate was collected, washed with water and dried to give 2.63 g. of 3-{(diethylamino)[4-(dimethylamino)phenyl]methyl}-1-ethyl-2-methyl-1H-indole, m.p. 128°–133° C.

C. A mixture containing 5.0 g. of 3-{[4-dimethylamino)phenyl](4-methylphenylsulfonyl)methyl}-1-ethyl-2-methyl-1H-indole, 15 ml. of N,N-diethylformamide and 75 ml. of 10% aqueous sodium hydroxide was heated 2 hours under reflux. The reaction mixture was then cooled and diluted with 50 ml. of water and the resulting solid was collected, washed with water and dried to give 3.7 g. of tan solid, m.p. 97°–103° C. Thin layer chromatography indicated this material to be essentially the same as the product of part B above. A toluene solution of this product when contacted with acidic clay developed a magenta image and when contacted with phenolic resin developed a purple image.

EXAMPLE 2

To a stirred mixture containing 5.4 g. (0.012 mole) of 3-{[4-(dimethylamino)phenyl](4-methylphenylsulfonyl)methyl}-1-ethyl-2-methyl-1H-indole, 20 ml. of m-chloroaniline and 1 g. of benzyltriethylammonium chloride in 50 ml. of dichloromethane was added dropwise 25 ml. of 25% aqueous sodium hydroxide. When the addition was complete, the reaction mixture was heated under reflux for about 2.5 hours and then partitioned between 400 ml. of water and 300 ml. of toluene. The organic layer was separated and steam-distilled until the distillate was clear. The residue was cooled and the reddish-brown solid was collected by filtration; washed with hexane and dried. Crystallization from 200 ml. of 2-propanol afforded 0.3 g. of 3-{(m-chloroanilino)[4-(dimethylamino)phenyl]methyl}-1-ethyl-2-methyl-1H-indole as a tan solid which softened at 109°–125° C. and melted at 147°–149° C. with decomposition. A toluene solution of this material when contacted with acidic clay developed a bluish-red image and when contacted with phenolic resin developed a purple image. Evaporation of the filtrate left a gummy residue. Thin layer chromatography indicated the major component of this residue to be identical to the isolated product.

EXAMPLE 3

A mixture containing 5.0 g. of 3-{[4-(dimethylamino)phenyl](4-methylphenylsulfonyl)methyl}-1-ethyl-2-methyl-1H-indole, 50 ml. of 20% aqueous sodium hydroxide and 10 ml. of N,N-dimethylformamide was heated 2 hours at about 40°–45° C. The reaction mixture was then diluted with 100 ml. of ice-water and the resulting solid was collected, washed with water and dried to give 3.64 g. of 3-{(dimethylamino)[4-(dimethylamino)phenyl]methyl}-1-ethyl-2-methyl-1H-indole, m.p. 144°–146° C. A toluene solution of this product when contacted with acidic clay or phenolic resin developed a bluish-red image.

EXAMPLE 4

A. To a stirred mixture containing 5.0 ml. of concentrated hydrochloric acid, 35 ml. of ethyl alcohol, 6.2 g. of 85.9% sodium p-toluenesulfinate and 4.5 g. of 94.4% 1-ethyl-2-methyl-1H-indole was added 2.8 g. of thiophene-2-carboxaldehyde. After stirring approximately one hour at 55°–60° C. the reaction mixture was cooled to about 40° C. and then diluted with 25 ml. of ethyl alcohol followed by 300 ml. of water and 200 g. of ice. The resulting solid was collected by filtration and washed with water. The product was suspended in 60 ml. of cold 2-propanol containing sufficient ammonium hydroxide to maintain a slightly alkaline condition and the resulting suspension was stirred approximately 45 minutes at 5°–10° C. The solid was then collected by filtration, washed with fresh 2-propanol and dried under vacuum at 45° C. to afford 10.0 g. of 3-[(4-methylphenylsulfonyl)(2-thienyl)methyl]-1-ethyl-2-methyl-1H-indole, m.p. 168°–169° C. (dec.).

B. Following a procedure similar to that described in Example 3 but employing 5.0 g. of 3-[(4-methylphenylsulfonyl)(2-thienyl)methyl]-1-ethyl-2-methyl-1H-indole, 50 ml. of 20% aqueous sodium hydroxide and 10 ml. of N,N-dimethylformamide, there was obtained 4.1 g. of 3-[(dimethylamino)(2-thienyl)methyl]-1-ethyl-2-methyl-1H-indole, m.p. 126°–129° C. A toluene solution of this product when contacted with acidic clay developed a yellow image.

EXAMPLE 5

A. Following a procedure similar to that described in Example 4A but employing 6.5 g. of 81.9% sodium p-toluenesulfinate, 6.3 g. of 95% 4-(benzylethylamino)benzaldehyde and 3.8 g. of 86.1% 1-ethyl-2-methyl-1H-indole, there was obtained 15.3 g. of 3-{[4-(benzylethylamino)phenyl](4-methylphenylsulfonyl)methyl}-1-ethyl-2-methyl-1H-indole as a gray tar-like product.

B. Following a procedure similar to that described in Example 3 but employing 8.0 g. of 3-{[4-(benzylethylamino)phenyl](4-methylphenylsulfonyl)methyl}-1-ethyl-2-methyl-1H-indole, 60 ml. of 20% aqueous sodium hydroxide and 20 ml. of N,N-dimethylformamide, there was obtained 4.7 g. of 3-{[4-(benzylethylamino)phenyl](dimethylamino)methyl}-1-ethyl-2-methyl-1H-indole, m.p. 120°–125° C. A toluene solution of this product when contacted with acidic clay developed a bluish-red image and when contacted with phenolic resin developed a violet image.

EXAMPLE 6

Following a procedure similar to that described in Example 3 but employing 6.0 g. of 3-{[4-(dimethylamino)phenyl](4-methylphenylsulfonyl)methyl}-1-ethyl-2-methyl-1H-indole, 10 ml. of 1-formylpiperidine and 50 ml. of 20% aqueous sodium hydroxide, there was obtained 4.3 g. of 3-{[4-(dimethylamino)phenyl](1-piperidinyl)methyl}-1-ethyl-2-methyl-1H-indole which softened at 153° C. and melted at 158°–160° C. A toluene solution of this product when contacted with acidic clay developed a bluish-red image and when contacted with phenolic resin developed a violet image.

EXAMPLE 7

A. Following a procedure similar to that described in Example 4A but employing 6.5 g. of 85.9% sodium p-toluenesulfinate 4.6 g. of 1-ethyl-2-methyl-1H-indole-3-carboxaldehyde and 3.8 g. of 1-ethyl-2-methyl-1H-indole there was obtained 4.5 g. of 3-[(1-ehtyl-2-methyl-1H-indol-3-yl)(4-methylphenylsulfonyl)methyl]-1-ethyl-2-methyl-1H-indole, m.p. 146°–152° C.

B. Following a procedure similar to that described in Example 3 but employing 3.0 g. of 3-[(1-ethyl-2-methyl-1H-indol-3-yl)(4-methylphenylsulfonyl)methyl]-1-ethyl-2-methyl-1H-indole, 50 ml. of 20% aqueous sodium hydroxide and 10 ml. of N,N-dimethylformamide, there was obtained 2.1 g. of 3-[(dimethylamino)(1-ethyl-2-methyl-1H-indol-3-yl)methyl]-1-ethyl-2-methyl-1H-indole, m.p. 154°–156° C. A toluene solution of this product when contacted with acidic clay or phenolic resin developed an orange image.

EXAMPLE 8

Following a procedure similar to that described in Example 3 but employing 5.0 g. of 3-{[4-(dimethylamino)phenyl](4-methylphenylsulfonyl)methyl}-1-ethyl-2-methyl-1H-indole, 15 ml. of 1-formylmorpholine and 75 ml. of 10% aqueous sodium hydroxide, there was obtained 4.5 g. of 3-{[4-(dimethylamino)phenyl](1-morpholino)methyl}-1-ethyl-2-methyl-1H-indole, m.p. 108°–113° C. A toluene solution of this product when contacted with acidic clay developed a magenta image and when contacted with phenolic resin developed a purple image.

EXAMPLE 9

A. Following a procedure similar to that described in Example 4A but employing 6.5 g. of 81.9% sodium p-toluenesulfinate, 2.4 g. of furfural and 3.8 g. of 86.1%. 1-ethyl-2-methyl-1H-indole there was obtained 4.5 g. of 3-[(2-furyl)(4-methylphenylsulfonyl)methyl]-1-ethyl-2-methyl-1H-indole, m.p. 144°–146° C.

B. Following a procedure similar to that described in Example 3 but employing 5.0 g. of 3-[(2-furyl)(4-methylphenylsulfonyl)methyl]-1-ethyl-2-methyl-1H-indole, 100 ml. of 15% aqueous sodium hydroxide and 10 ml. of N,N-dimethylformamide, there was obtained 3.7 g. of 3-[(dimethylamino)(2-furyl)methyl]-1-ethyl-2-methyl-1H-indole, m.p. 110.5°–115° C. A toluene solution of this product when contacted with acidic clay or phenolic resin developed a yellow image.

EXAMPLE 10

A mixture containing 5.0 g. of 3-{4-(dimethylamino)phenyl](4-methylphenylsulfonyl)methyl}-1-ethyl-2-methyl-1H-indole, 10 ml. of N-methylformanilide and 50 ml. of 20% aqueous sodium hydroxide was heated 2 hours at 50° C. The reaction mixture was then cooled and diluted with 100 ml. of water followed by 50 ml. of hexane. After stirring for 10 minutes the resulting solid was collected, washed with water and hexane and dried to give 4.05 g. of 3-{[4-(dimethylamino)phenyl](methylphenylamino)methyl}-1-ethyl-2-methyl-1H-indole, m.p. 170°–172° C. A toluene solution of this product when contacted with acidic clay developed a bluish-red image and when contacted with phenolic resin developed a reddish-purple image.

EXAMPLE 11

Following a procedure similar to that described in Example 10 but employing 5.0 g. of 3-[(4-methylphenylsulfonyl)(2-thienyl)methyl]-1-ethyl-2-methyl-1H-indole, 8 ml. of formylpiperidine and 50 ml. of 20% aqueous sodium hydroxide, there was obtained 3.0 g. of 3-[(1-piperidinyl)(2-thienyl)methyl]-1-ethyl-2-methyl-1H-indole, m.p. 151°–153° C. A toluene solution of this product when contacted with acidic clay developed a yellow image.

EXAMPLE 12

A. Following a procedure similar to that described in Example 1A but employing 6.3 g. of 85% sodium p-toluenesulfinate, 2.2 g. of 98% 1-methylpyrrole-2-carboxaldehyde and 3.8 g. of 94% 1-ethyl-2-methyl-1H-indole, there was obtained 8.4 g. of 3-[(1-methyl-2-pyrrolyl)(4-methylphenylsulfonyl)methyl]-1-ethyl-2-methyl-1H-indole, m.p. 180° C.

B. A mixture containing 1.4 g. of 3-[(4-methylphenylsulfonyl)(1-methyl-2-pyrrolyl)methyl]-1-ethyl-2-methyl-1H-indole, 5 ml. of N,N-dimethylformamide and 30 ml. of 20% aqueous sodium hydroxide was heated 3 hours at 50° C. The reaction mixture was then cooled and diluted with 100 ml. of water and the product extracted with toluene. The toluene extracts were washed with water and evaporated to dryness affording 3-[(dimethylamino)(1-methyl-2-pyrrolyl)methyl]-1-ethyl-2-methyl-1H-indole as a brown gummy material, the infrared and nuclear magnetic resonance spectra of which were consistent with the assigned structure. A toluene solution of this product when contacted with acidic clay or phenolic resin developed an orange image.

EXAMPLE 13

A. Following a procedure similar to that described in Example 12B but employing 5.0 g. of 3-{[4-(dimethylamino)phenyl](4-methylphenylsulfonyl)methyl}-1-ethyl-2-methyl-1H-indole, 5 ml. of N-[3-(dimethylamino)propyl]formamide and 80 ml. of 15% aqueous sodium hydroxide, there was obtained 5.0 g. of 3-{[3-(dimethylamino)propylamino][4-(dimethylamino)phenyl]methyl}-1-ethyl-2-methyl-1H-indole as a pale yellow oil. A toluene solution of this product when contacted with acidic clay developed a red image and when contacted with phenolic resin developed a purple-red image.

B. Stirring for 0.5 hour, the mixture containing 1.4 g. of the product of part A above, 1 ml. of methyl iodide and 30 ml. of toluene, collecting the solid produced and washing with toluene afforded 1.4 g. of the corresponding methiodide as a brown solid which turned to a gummy tar upon standing in air. This product developed a magenta image on acidic clay and a purple image on phenolic resin.

It is contemplated that by following procedures similar to those described in the foregoing examples but employing the appropriate 1-$R_1$-2-$R_2$-3-[(R-phenylsulfonyl)(Z)methyl]-1H-indole, and the appropriate amine $R_3R_4NH$ or precursor thereof, there will be obtained the 1-$R_1$-2-$R_2$-3-[($R_3R_4N$)(Z)methyl]-1H-indoles of Formula I, Examples 14–25 presented in Table A hereinbelow:

TABLE A

| | 1-$R_1$—2-$R_2$—3-[($R_3R_4N$)(Z)methyl]-1H—indoles of Formula I | | | | |
| --- | --- | --- | --- | --- | --- |
| Ex. | $R_1$ | $R_2$ | $R_3$ | $R_4$ | Z |
| 14 | H | H | n-$C_4H_9$ | n-$C_4H_9$ | 4-(n-$C_4H_9$)$_2$N—$C_6H_4$ |
| 15 | $CH_3$ | $C_6H_5$ | H | p-$CH_3$—$C_6H_4$ | 4-$C_6H_5$—$C_6H_4$ |
| 16 | n-$C_4H_9$ | $CH_3$ | H | p-$CH_3O$—$C_6H_4$ | 1-naphthyl |
| 17 | $CH_3$ | $CH_3$ | —($CH_2$)$_4$— | | 2-Cl—4-($CH_3$)$_2$N—$C_6H_3$ |
| 18 | $CH_3$ | $CH_3$ | —($CH_2$)$_6$— | | 2-pyridyl |
| 19 | $C_2H_5$ | $CH_3$ | $CH_3$ | $CH_3$ | 1-$C_2H_5$—2-$CH_3$—indol-3-yl |
| 20 | H | $CH_3$ | $CH_3$ | p-Br—$C_6H_4$ | 2,4-[($CH_3$)$_2$N]$_2$—$C_6H_3$ |
| 21 | $C_2H_5$ | $C_2H_5$ | $CH_3$ | $C_2H_5$ | 2-$C_2H_5$O—4-($C_2H_5$)$_2$N—$C_6H_3$ |
| 22 | $CH_3$ | $CH_3$ | H | m-F—$C_6H_4$ | 2-$CH_3$—4-($CH_3$)$_2$N—$C_6H_3$ |
| 23 | $C_2H_5$ | $CH_3$ | $CH_3$ | $CH_3$ | 9-$C_2H_5$—carbazol-3-yl |
| 24 | H | $CH_3$ | H | p-($CH_3$)$_3$C—$C_6H_4$ | 2-F—4-($CH_3$)$_2$N—$C_6H_3$ |
| 25 | $C_2H_5$ | $CH_3$ | H | p-($CH_3$)$_2$CHO—$C_6H_4$ | p-($C_2H_5$)$_2$N—$C_6H_4$ |

EXAMPLE 26

The color formers of Examples 3 and 10 were microencapsulated and applied to a carbonless duplicating transfer sheet essentially as described in U.S. Pat. No. 4,000,087. A mixture of 3.9 g. of Epon 1002 (a solid epoxy resin commercially available from Shell Chemical Company) and 27.9 g. of dibutyl phthalate was warmed until a clear solution was obtained. After the solution had cooled to room temperature, 2.0 g. of the color former was added and the mixture was again warmed until a clear solution was obtained. The solution was then allowed to cool to room temperature. A mixture containing 6.5 g. of terephthaloyl chloride and 31.5 g. of dibutyl phthalate was warmed until a clear solution was obtained. After it had cooled to room temperature, this solution was combined with the previously prepared solution containing the color former and the resulting mixture was added to a solution containing 3.9 g. of polyvinyl alcohol in 167.0 g. of distilled water. The resulting mixture was emulsified under high shear agitation for approximately 2 minutes or until a dispersed phase particle size of about 5 to 6 microns was obtained. The emulsion was then stirred at about 300 to 500 rpm while a solution containing 3.7 g. of diethylenetriamine and 1.9 g. of sodium carbonate in 22 ml. of distilled water was added. Stirring was continued overnight. At this point the emulsion containing the encapsulated color former of Example 3 had a stable pH of 7.6, whereas that of Example 10 had a pH of 6.2 which was adjusted to pH 7.3 with 15% aqueous sodium carbonate. The emulsion was then applied to a bond paper sheet (transfer sheet) at a coating weight of approximately 2.34 to 3.04 g. per square meter and the coated sheet was dried at 100° C. for approximately 30 to 45 seconds. The coated side of the transfer sheet was placed in contact with a receiving sheet coated with acidic clay or phenolic resin. Writing on the transfer sheet produced a violet duplicate image on the receiving sheet.

EXAMPLE 27

The color former of Example 6 was incorporated in a thermal paper essentially according to the procedure described in U.S. Pat. No. 3,539,375. A polyvinyl alcohol dispersion of the color former of Example 6 was prepared by shaking one hour on a paint shaker a mixture containing 2.0 g. of the color former, 3.7 g. of water, 8.6 g. of 10% aqueous polyvinyl alcohol and 10 ml. of zirconium grinding beads. A polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied at a thickness of 0.0015 inch to white paper sheets and the sheets were dried at room temperature. Contacting the coated sheets with a heated stylus at temperatures between 100° C. and 150° C. produced a violet to deep blue-violet image.

We claim:
1. A compound selected from the group consisting of 3-[(dimethylamino)(2-thienyl)methyl]-1-ethyl-2-methyl-1H-indole, and
3-[(1-piperidinyl)(2-thienyl)methyl]-1-ethyl-2-methyl-1H-indole.

* * * * *